United States Patent [19]

Tsukagoshi

[11] Patent Number: 4,708,137
[45] Date of Patent: Nov. 24, 1987

[54] HIGH-FREQUENCY INCISION DEVICE
[75] Inventor: Tsuyoshi Tsukagoshi, Tokyo, Japan
[73] Assignee: Olympus Optical Co., Ltd., Tokyo, Japan
[21] Appl. No.: 863,234
[22] Filed: May 14, 1986
[30] Foreign Application Priority Data May 20, 1985 [JP] Japan .............................. 60-74816[U]
Sep. 17, 1985 [JP] Japan ............................ 60-141806[U]

[51] Int. Cl.⁴ ............................................ A61B 17/36
[52] U.S. Cl. .......................... 128/303.15; 128/303.17
[58] Field of Search ... 128/4, 6, 303.1, 303.13–303.19, 128/305–314, 786, 790

[56] References Cited

U.S. PATENT DOCUMENTS

| | | | |
|---|---|---|---|
| 3,306,297 | 2/1967 | Voorhees et al. | 128/305.3 |
| 3,799,168 | 3/1974 | Peters | 128/303.14 |
| 3,910,279 | 10/1975 | Okada et al. | 128/303.15 |
| 4,043,342 | 8/1977 | Morrison | 128/303.14 |
| 4,181,131 | 1/1980 | Ogiu | 128/303.15 |
| 4,295,467 | 10/1981 | Mann et al. | 128/303.18 |
| 4,311,143 | 1/1982 | Komiga | 128/303.15 |
| 4,311,144 | 1/1982 | Harada | 128/303.15 |
| 4,485,812 | 12/1984 | Harada et al. | 128/303.15 |
| 4,503,855 | 3/1985 | Maskenka | 128/303.15 |
| 4,580,564 | 4/1986 | Andersen | 128/314 |

Primary Examiner—William E. Kamm
Assistant Examiner—Max F. Hindenburg

[57] ABSTRACT

A high-frequency incision device has a flexible sheath adapted to be inserted into the patient's body through the insertion channel of an endoscope. An end member is fixed to the distal end of the sheath and has a through hole extending in the axial direction of the sheath. The hole has a small diameter section on the side of the distal end of the sheath, a large diameter section, and a shoulder defined between the sections. A knife for piercing a desired portion is inserted through the hole to be capable of being project from and retreated into the sheath. The knife has a stopper portion integrally formed therewith and having a width greater than the small diameter section and smaller than the large diameter section. The stopper portion restricts the extent of projection of the knife cooperating with the shoulder. The knife is connected to a high-frequency power source through an operating wire.

8 Claims, 11 Drawing Figures

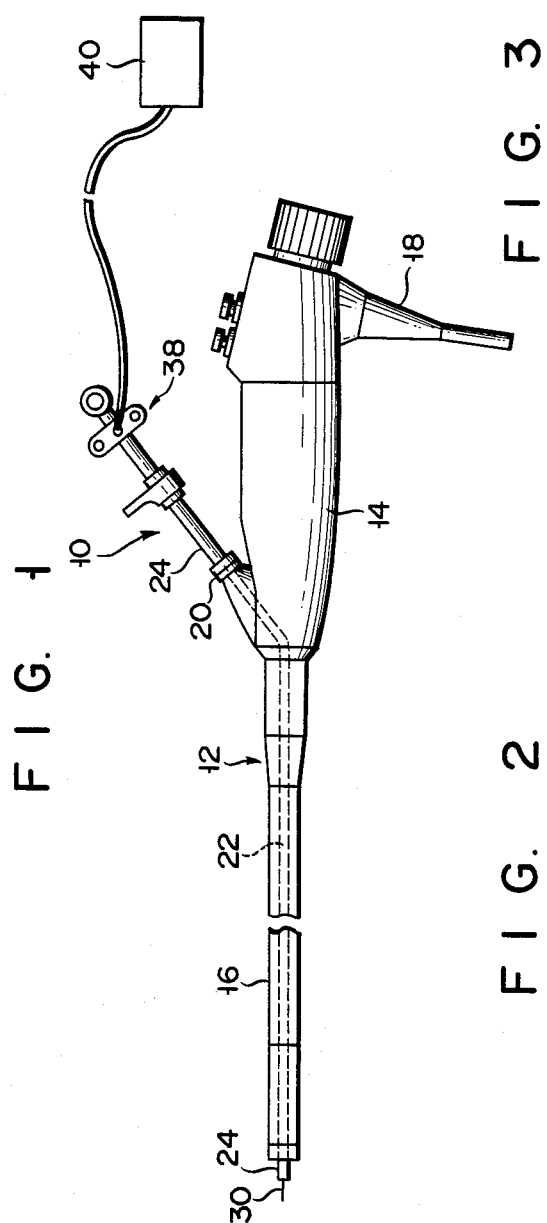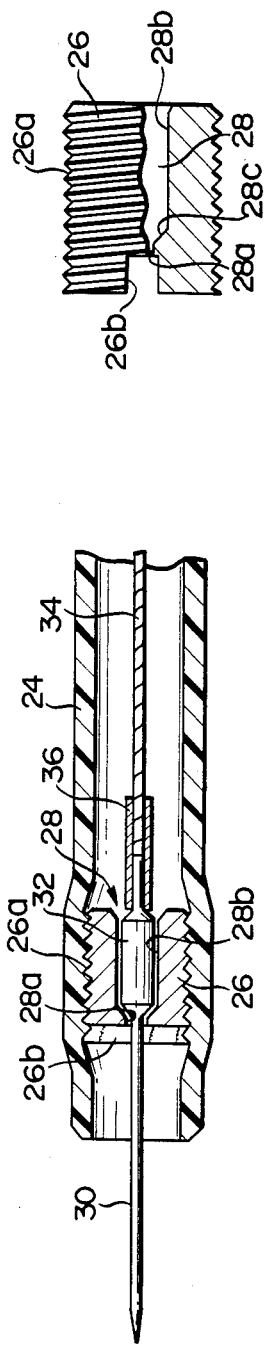

HIGH-FREQUENCY INCISION DEVICE

BACKGROUND OF THE INVENTION

This invention relates to a high-frequency incision device, which is inserted into the patient's body through the insertion channel of an endoscope, for performing high-frequency incision of the tissue in the patient's body.

Recently, high-frequency incision devices for performing incision of the tissue in the patient's body have been proposed to replace knives and scissors. Such a high-frequency incision device has a flexible tube which is electrically insulating, and an end member having an axial through hole is secured to the distal end of the tube. A metal needle, i.e., knife, can be projected from the end of the tube through the through hole. The knife is pushed out and pulled in from the proximal end of the tube via an operating wire extending through the tube. A high frequency current is supplied to the knife through the operating wire. The knife is provided with a stopper soldered to its intermediate portion and having a diameter greater than the diameter of the through hole. The stopper restricts the extent to which the knife is projected from the end member. Excessive projection of the knife is prevented, and so is excessive cutting of the tissue of the patient's body, is thus prevented.

With the incision device of this structure, however, when the knife is heated by heat produced by the high frequency current, it is liable that the solder is melted to result in detachment of the stopper from the knife. If the stopper is detached, the knife will now project excessively from the tube end into the tissue, thus leading to excessive cutting of the tissue. In addition, there is a risk that the knife falls into the patient's body.

SUMMARY OF THE INVENTION

The invention has been intended in the light of the above affairs, and its object is to provide a high-frequency incision device, which can reliably restrict the extent of projection of the knife and also prevent falling of the knife into the patient's body.

To attain the above object of the invention, there is provided a high frequency incision device, in which restricting means for restricting the extent of projection of the knife is integrally formed with the knife and has a greater width than the minimum diameter of the through hole formed in the end member.

With the incision device according to the invention, restricting means for restricting the extent of projection of the knife includes an engagement portion integral with the knife and having an increased width with respect to the rest of the knife and a stopper tube fitted on a portion of the knife inclusive of the engagement portion. The stopper tube has an outer diameter greater than the minimum diameter of the through hole of the end member, and its bore has a large diameter section corresponding to the engagement portion and a small diameter section nearer the distal end of the knife than the large diameter section.

BRIEF DESCRIPTION OF THE DRAWINGS

FIGS. 1 to 3 show a high-frequency incision device according to a first embodiment of the invention, in which FIG. 1 is a side view of the device which being inserted into an endoscope, FIG. 2 is a longitudinal sectional view showing a distal end portion of the device, and FIG. 3 is a side view, partly broken away, showing an end member;

DETAILED DESCRIPTION OF THE PREFERRED EMBODIMENTS

Figure 4:
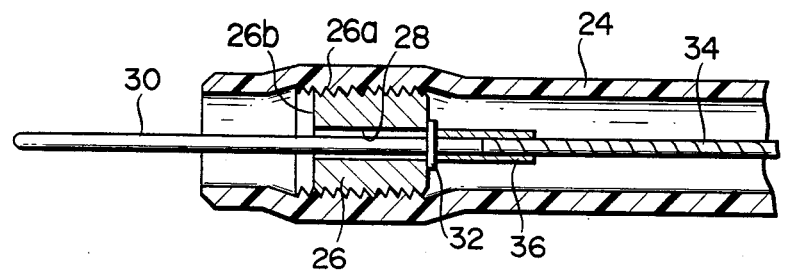
FIG. 4 is a longitudinal sectional view showing a distal end portion of an incision device according to a second embodiment of the invention.

Now, preferred embodiments of the invention will be described in detail with reference to the drawings.

FIG. 1 shows endoscope 12, in which high-frequency incision device 10 according to the invention is inserted. Endoscope 12 has operation section 14, insertion section 16 and universal cord 18 both extending from the operation section. Insertion channel 22 is provided in insertion section 16, and has one end open at the distal end face of the insertion section and the other end connected to an inlet port 20 formed in operation section 14.

Incision device 10 has soft sheath 24 made of an electrically insulating material, e.g., "Teflon" (tradename). Sheath 24 has a smaller outer diameter than the inner diameter of insertion channel 22. It is inserted into the insertion channel through inlet port 20. As shown in FIGS. 2 and 3, cylindrical end member 26 made of an electrically insulating material is fitted in an end portion of sheath 24 at a position thereof slightly retreated form the end. End member 26 has threaded portion 26a formed on the outer periphery, and its end face is formed with groove 26b, in which a drive or the like may be engaged. End member 26 is screwed in sheath 24. It has through hole 28 which is coaxial with sheath 24. Through hole 28 has small diameter section 28a on the side of the distal end of sheath 24 and large diameter section 28b on the side of the proximal end of the sheath. Shoulder 28c is formed between the small and large diameter sections. Elongate knife 30 made of stainless steel and having a pointed end is slidably inserted into through hole 28. The distal end portion of knife 30 can be projected from and retreated into sheath 24 with movement of the knife through the through hole. The proximal end portion of knife 30 has a greater diameter than that of the other portion thereof, or the inner diameter of small diameter section 28a of through hole 28 and constitutes stopper portion 32. Stopper portion 32 has a slightly smaller diameter than the inner diameter of large diameter section 28b of through hole 28. When knife 30 is moved in the direction to project from sheath 24, stopper portion 32 strikes shoulder 28c of through hole 28 to restrict the extent of projection of knife from the sheath end.

Operating wire 34 which is slidably inserted in sheath 24 has one end soldered to the proximal end of knife 30 via joint tube 36. The other end of wire 34 is connected to operating mechanism 38 provided on the base end of sheath 24. Knife 30 can be projected from and retreated into sheath 24 with operating wire 34 pushed or pulled by operating mechanism 38. High frequency power source 40 is connected to the other end of operating wire 34.

The operation of the incision device having the above construction will now be described.

First, insertion section 16 of endoscope 12 is inserted into the patient's body. Then, sheath 24 of device 10 is inserted into insertion channel 22 of the endoscope. Sheath 24 is inserted until its distal end slightly projects from the distal end of insertion section 16. At this time, the distal end of knife 30 is found in sheath 24. In this state, the distal end of insertion section 16 is operated from operating section 14 to bring the distal end of sheath 24 to the neighborhood of the surface of tissue to be cut. Subsequently, operating wire 34 is pushed in by operating mechanism 38, whereby knife 30 is projected from the distal end of sheath 24 into the tissue. The extent of projection of knife 30 is restricted by stopper portion 32. Thus, the knife will never excessively project. Knife 30 is moved by operating the distal end of insertion section 16 while supplying high-frequency current to knife 30 from high-frequency power source 40 through operating wire 34, thereby the tissue is high-frequency cut.

With the incision device having the above construction, the extent of projection of knife 30 from the distal end of sheath 24 at the time of the high-frequency incision of the tissue, is restricted as stopper portion 32 of the knife strikes shoulder 28c of through hole 28. The knife, therefore, will never be excessively projected. It is thus possible to eliminate an accident of excessively cutting the tissue with excessive projection of knife 30 during the incision operation. If the output of the high-frequency power source is excessive or in case when current is supplied for long time in the incision operation, heat is greatly produced between the tissue surface and end of knife 30 and transferred to the proximal end portion of the knife. However, since stopper portion 32 is integral with knife 30, unlike the stopper soldered to the knife in the prior art, it will never detached from the knife due to heat. In a further aspect, it is liable that heat noted above is transferred to joint tube 36 to cause melting of solder, leading to detachment of knife 30 from operating wire 34. With this embodiment, even if knife 30 is detached from operating wire 34, stopper portion 32 thereof can not pass through small diameter section 28a of through hole 28. Thus, there is no possibility for the knife to escape from end member 26 and sheath 24 and fall into the patient's body or be excessively projected.

FIG. 4 shows a second embodiment of the invention. This embodiment is different from the preceding first embodiment in the shape of knife 30 and through hole 28. In this embodiment, through hole 28 has a fixed diameter over its entire length. Knife 30 has rounded distal end and has integral, flange-like stopper portion 32 at the proximal end portion thereof. Stopper portion 32 has a greater diameter than the inner diameter of through hole 28. The extent of projection of knife 30 is restricted as stopper portion 32 strikes the rear end surface of end member 26.

With the second embodiment, the same effects as in the first embodiment can be obtained.

Figure 5:
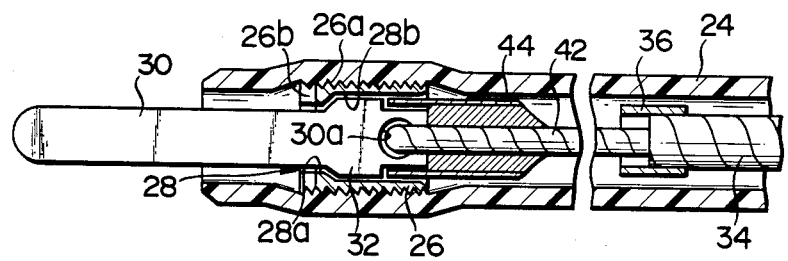
FIGS. 5 and 6 are longitudinal sectional views taken in different directions showing a distal end portion of an incision device according to a third embodiment of the invention.
Figure 6:
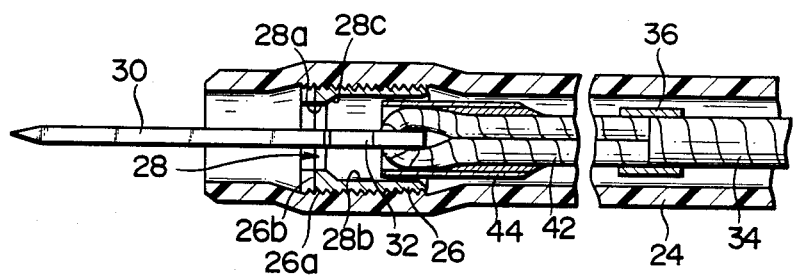

FIGS. 5 and 6 show a third embodiment of the invention. In this embodiment, like the previous first embodiment, end member 26 has through hole 28 having small diameter section 28a on the side of the distal end of sheath 24 and large diameter section 28b on the side of the proximal end of the sheath. Shoulder 28c is defined between the small and large diameter sections. Knife 30 is made from a thin plate or strip having a width slightly smaller than the diameter of small section 28a of through hole 28. A proximal end portion of the knife has a greater width than the diameter of small diameter section 28a and constitutes stopper portion 32. The proximal end portion of knife 30 has hole 30a, through which connecting wire 42 is inserted. Wire 42 is folded at hole 30a, and its opposite ends are coupled to the end of operating wire 34 by joint tube 36. Retainer tube 44 is fitted around the folded portion of connecting wire 42. Retainer tube 44 is soldered to the connecting wire and knife.

With this third embodiment having the above construction, like the above embodiments, the extent of projection of the knife is restricted by stopper portion 32. Further, even when solder is melted due to heating of knife 30, the knife is never disconnected from connecting wire 42 and can be reliably advanced and retreated through operating wire 34. Further, after the incision operation is ended, the sheath can be withdrawn from the insertion channel with knife 30 held retracted in sheath 24. Thus, the sheath can be withdrawn without causing damage to the insertion channel.

Figure 7:
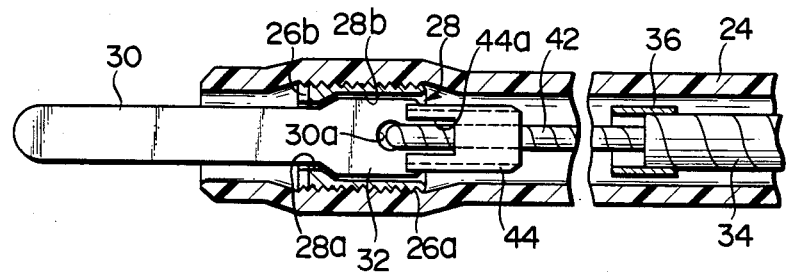
FIGS. 7 and 8 are longitudinal sectional views taken in different directions showing a distal end portion of an incision device according to a fourth embodiment of the invention.
Figure 8:
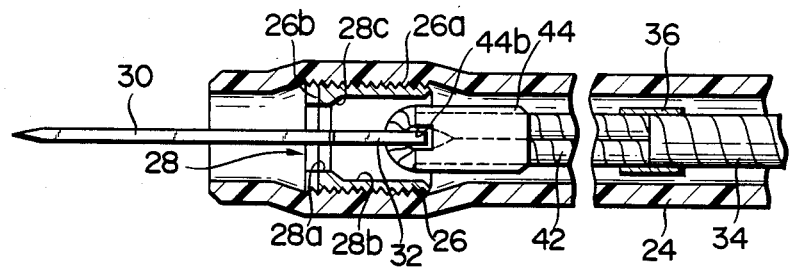

FIGS. 7 and 8 show a fourth embodiment. This embodiment is substantially the same as the third embodiment, and is different only in that retainer tube 44 has a pair of first grooves 44a for accommodating the folded portion of connecting wire 42 and a pair of second grooves 44b for accommodating the rear end of knife 30. With this construction, knife 30 can be secured to connecting wire 42 by retainer tube 44 without use of solder. In addition, the diameter of retainer tube 44 can be reduced, thereby permitting smooth advancement and retreat of operating wire 34 and knife 30 through sheath 24. Further, it is possible to reduce resistance offered against flow in sheath 24 when pouring liquid, e.g., an image forming agent or rinsing liquid, through sheath 24.

Figure 9:
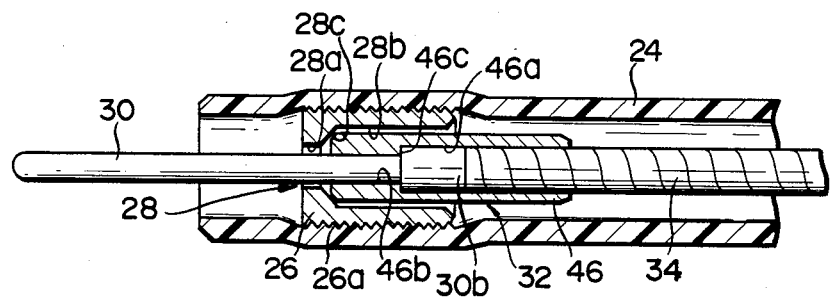
FIGS. 9 to 11 are longitudinal sectional views showing distal end portions of incision devices according to fifth to seventh embodiments of the invention. de

FIG. 9 shows a fifth embodiment of the invention. This embodiment is different from the first embodiment in the structure of stopper portion 32. In FIG. 9, parts like those in FIG. 2 are designated by like reference numerals, and description of these parts is omitted. In this embodiment, the proximal end portion of knife 30 has a greater diameter than the rest of the knife and constitutes engagement portion 30b. Stopper tube 46 is fitted on the proximal end portion of the knife. Stopper tube 46 has an outer diameter, which is greater than small diameter section 28a of through hole 28 in end member 26 and is slightly smaller than the diameter of large diameter section 28b. The bore of stopper tube 46 has large diameter section 46a having a diameter equal to the outer diameter of engagement portion 30b of knife 30 and small diameter section 46b having a diameter equal to the diameter of the rest of the knife. Shoulder 46c is defined between the large and small diameter sections. Knife 30 is prevented form being detached forwardly from stopper tube 46 as the end of engagement portion 30b of it abuts shoulder 46c of stopper tube 46. Stopper tube 46 abuts shoulder 28c of end member 26 at its end, thus restricting the extent of projection of knife 30. Stopper portion 32 is thus constructed by stopper tube 46 and engagement portion 30b. Stopper tube 46 extends rearwardly beyond the proximal end of knife 30, and an end portion of operating wire 34 is inserted in the rear end portion of the stopper tube. Stopper tube 46 is secured by solder to operating wire 34. That is, stopper tube 46 also serves the joint tube in the first embodiment.

With the fifth embodiment having the above construction, the extent of projection of knife 30 is restricted by stopper portion 32, so that it is impossible for the knife to project excessively during an incision operation. Further, even if knife 30 is detached from operating wire 34 due to melting of solder caused by heat produced by the high-frequency incision operation, the knife will never fall into the patient's body.

Figure 10:
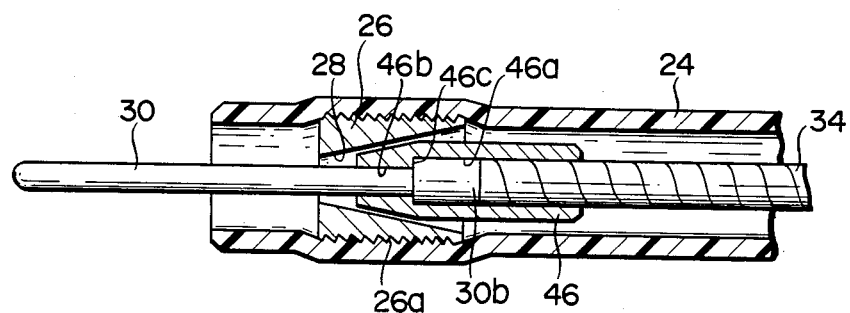

FIG. 10 shows a sixth embodiment. This embodiment is different from the fifth embodiment in the shape of through hole 28 of end member 26 and the shape of stopper tube 46. More specifically, through hole 28 is tapered toward the distal end of sheath 24. The distal end portion of the outer periphery of stopper tube 46 also has a taper similar to the taper of the through hole.

With this construction, when knife 30 is projected, the surface of through hole 28 and corresponding outer periphery of stopper tube 46 are held in close contact with each other to prevent rattling of the knife or projection thereof in an oblique direction form sheath 24, as well as restricting the extent of projection of the knife. The incision operation thus can be performed safely and reliably.

Figure 11:
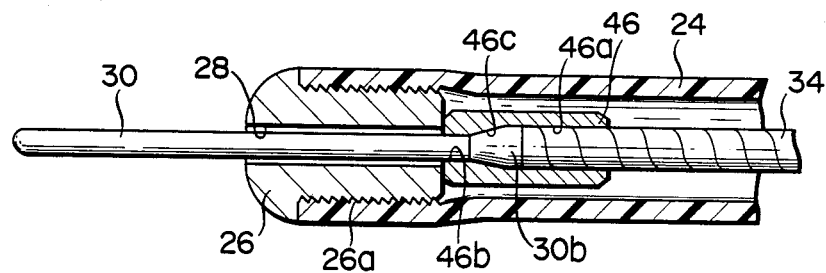

FIG. 11 shows a seventh embodiment of the invention. In this embodiment, end member 26 is secured to the distal end of sheath 24, and through hole 28 has a fixed inner diameter over the entire length of end member 26. Further, engagement portion 30b of knife 30 is tapered toward the distal end of sheath 24. With this embodiment, the extent of projection of the knife is restricted as the end of stopper tube 46 abuts the rear end of end member 26. Further, there is no possibility of clogging of the distal end of sheath 24 with tissue pieces, viscous liquid, blood, etc. Furthermore, the incision device can be easily washed.

The present invention is not limited to the above embodiments and various changes and modifications may be effected therein by one skilled in the art without departing from the scope of the invention. For example, knife 30 need not be made of stainless steel, but it may be made of a magnetic material as well. In this case, in an event when knife 30 is broken and the broken piece thereof falls into the patient's body during operation of bending the inserting section of the endoscope, the broken piece may be readily recovered from the patient's body with a recovery tool having a magnet. Further, instead of screwing end member 26 into sheath 24, it may be pressure fitted in or fusedly secured to the sheath. Further, the end member may be made of a conductive material. e.g., SUS stainless steel.

What is claimed is:

1. A high frequency incision device comprising: an elongated flexible sheath for insertion into a patient's body through an insertion channel of an endosoope; said sheath having a distal end, a proximal end and electrical insulating capability;
    an end member fixed to said sheath at a location slightly removed from the distal end toward to proximal end of the sheath, the end member having a through hole extending in axial direction of the sheath;
    a knife slidably inserted through the through hole, for incising a desired portion of tissue in the patient's body by means of a high-frequency current from a high-frequency power source, said knife having a stopper portion which is integrally formed with the knife and has a width greater than the minimum diameter of the through hole to restrict the extent of projection of the knife from the end member;
    an operating wire movably inserted through the sheath, said wire having one end connected to the knife, and another end connected to the high-frequency power source for conducting high-frequency current from the high-frequency power source to the knife; and
    means connected to the wire between the proximal end of the sheath and the power source, for advancing and retracting the knife with respect to the distal end of the sheath.

2. The high-frequency incision device according to claim 1, wherein said through hole has a small diameter section on the side of the distal end of the sheath, a large diameter section on the side of the proximal end of the sheath, and a shoulder defined between the small and large diameter sections, said stopper portion having a width greater than the diameter of the small diameter section and smaller than the diameter of the large diameter section and being cooperative with the shoulder to restrict the extent of projection of the knife.

3. The high-frequency incision device according to claim 1, wherein said knife has a hole formed in the proximal end portion, and said operating wire includes a first wire passed through and folded at the hole and a second wire having one end connected to the opposite ends of the first wire and the other end connected to the high-frequency power source.

4. The high-frequency incision device according to claim 3, which further comprises a retainer tube fitted around the folded portion of the first wire.

5. A high-frequency incision device comprising: an elongated flexible sheath for insertion into a patient's body through an insertion channel of an endoscope; and sheath having a distal end, a proximal end and electrical insulating capability;
    an end member fixed to said sheath at a location slightly removed from the distal end toward the proximal end of the sheath, the end member having a through hole extending in axial direction of the sheath;
    a knife slidably inserted through the through hole, for incising a desired portion of tissue in the patient's body by means of a high-frequency current from a high-frequency power source, said knife having a stopper portion which is integrally formed with the knife and has a width greater than the minimum diameter of the through hole to restrict the extent of projection of the knife from the end member;
    restricting means for restricting the extent of projection of the knife from the distal end of the sheath, said means including a stopper tube fitted on one part of the knife, having an outer diameter greater than the minimum diameter of the through hole and being cooperative with the end member to restrict the extent of projection of said knife, and an engagement portion formed on said one part of the knife for engaging with the inner surface of the stopper tube to restrict the movement of the knife in the projecting direction with respect to the stopper tube;
    an operating wire movably inserted through the sheath, said wire having one end connected to the knife, and another end connected to the high-frequency power source for conducting high-frequency current from the high-frequency power source to the knife; and means connected to the wire between the proximal end of the sheath and the power source, for advancing and retracting the knife with respect to the distal end of the sheath.

6. The high-frequency incision device according to claim 5, wherein said through hole has a small diameter section on the side of the distal end of the sheath, a large diameter section on the side of the proximal end of the sheath, and a shoulder defined between the small and large diameter sections, said stopper tube having an outer diameter greater than the diameter of the small diameter section and smaller than the diameter of the large diameter section and being cooperative with the shoulder to restrict the extent of projection of the knife.

7. The high-frequency incision device according to claim 5, wherein said engagement portion has a width greater than the the width of the rest of the knife, and the bore of said stopper tube has a large diameter section having a diameter equal to the width of the engagement portion, a small diameter section nearer the distal end of the sheath than the large diameter section and having a diameter smaller than the diameter of the large diameter section, and a shoulder defined between the large and small diameter sections, said engagement portion being cooperative with the shoulder to restrict the movement of the knife in the projecting direction with respect to the stopper tube.

8. The high-frequency incision device according to claim 5, wherein said through hole is tapered toward the distal end of the sheath, and the outer periphery of that portion of the stopper tube which is located on the side of the distal end of the sheath has a taper similar to the taper of the through hole.

* * * * *